United States Patent [19]

Yuhda

[11] Patent Number: 4,800,156
[45] Date of Patent: Jan. 24, 1989

[54] ANAEROBIC GERMICULTURE RECEPTACLE

[75] Inventor: Sadayuki Yuhda, Kawanishi, Japan

[73] Assignee: Sankin Kogyo Kabushiki Kaisha, Osaka, Japan

[21] Appl. No.: 69,191

[22] Filed: Jul. 2, 1987

Related U.S. Application Data

[63] Continuation-in-part of Ser. No. 854,611, Apr. 22, 1986, abandoned.

[30] Foreign Application Priority Data

Apr. 25, 1985 [JP] Japan .................................. 60-89698

[51] Int. Cl.⁴ .............................................. C12M 1/24
[52] U.S. Cl. ...................................... 435/296; 435/801; 215/321; 215/354
[58] Field of Search ................ 435/253, 287, 296, 801, 435/807; 215/6, 354, 276, 321; 220/23; 422/102, 120

[56] References Cited

U.S. PATENT DOCUMENTS

| | | | |
|---|---|---|---|
| 1,077,538 | 11/1913 | Magni | 215/321 |
| 2,620,938 | 12/1952 | Jesnig | 215/321 |
| 3,191,790 | 6/1965 | Coven et al. | 215/354 |

FOREIGN PATENT DOCUMENTS 144931 2/1985 Japan .................................. 435/296

Primary Examiner—Samuel Scott
Assistant Examiner—Noah Kamen
Attorney, Agent, or Firm—Oblon, Fisher, Spivak, McClelland & Maier

[57] ABSTRACT

An anaerobic germiculture receptacle comprises a first receptacle and a second receptacle accommodated in the first receptacle; a sealing plug securing the seal against the first receptacle, the sealing plug including a bore in which the second receptacle is held; and a pushing rod insertable in the bore so as to push the second receptacle down, wherein all operation is safely carried out without breaking the air-tight arrangement.

2 Claims, 4 Drawing Sheets

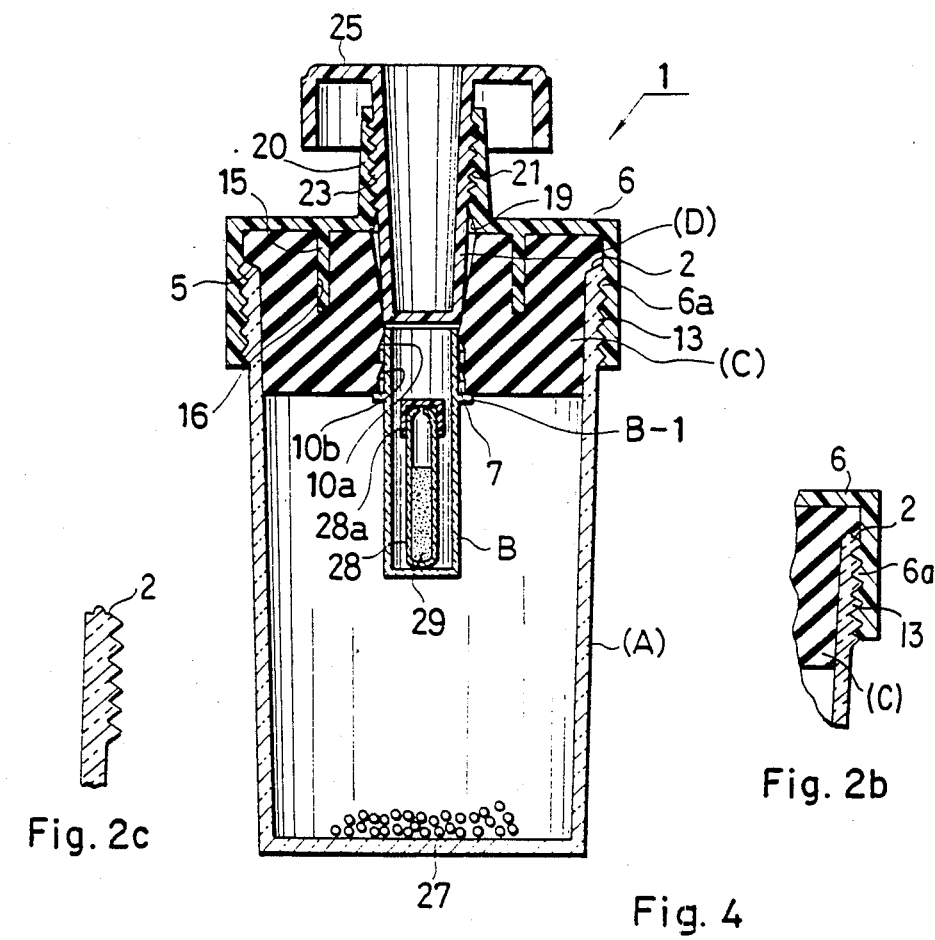
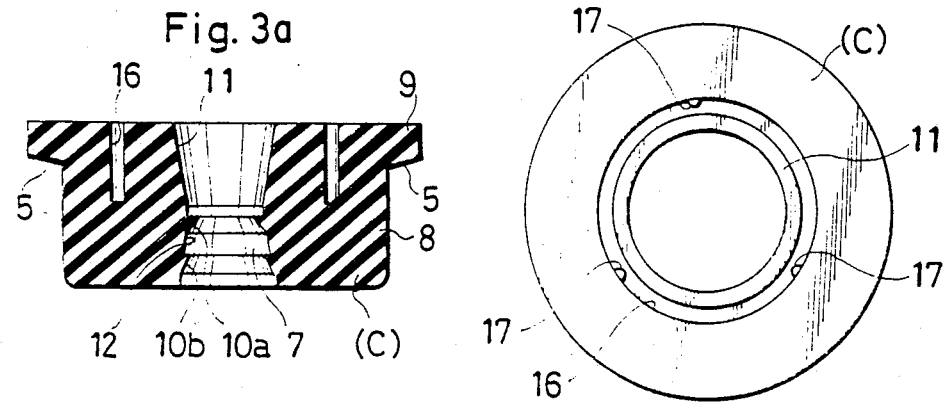

Fig. 5a
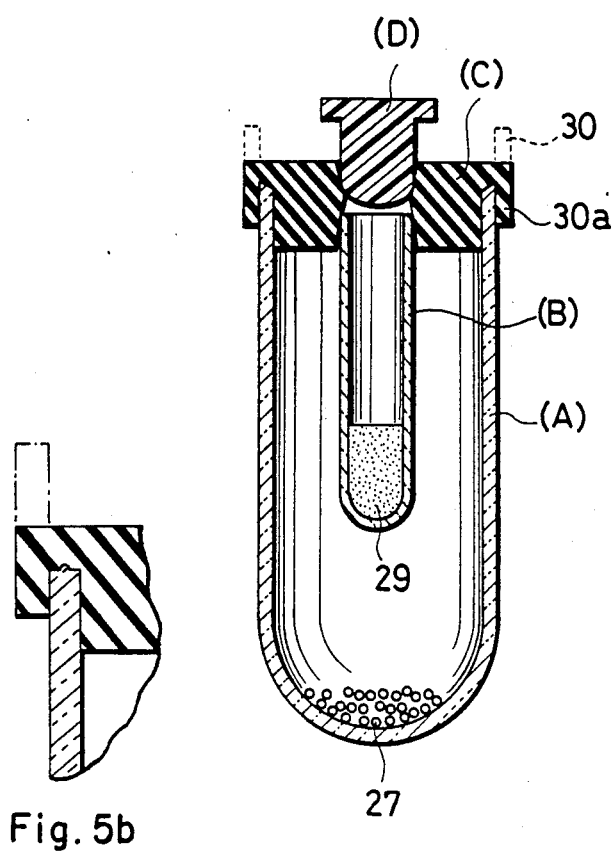
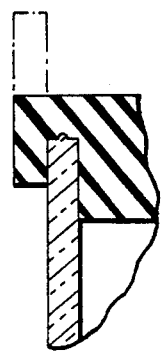
Fig. 5b

ANAEROBIC GERMICULTURE RECEPTACLE

RELATED APPLICATIONS

This application is a continuation-in-part application of copending Ser. No. 06/854,611 filed Apr. 22, 1986, now abandoned.

BACKGROUND OF THE INVENTION

1. Field of the Invention

The present invention relates to an anaerobic germiculture receptacle which enables anaerobic germs to be readily cultured.

2. Discussion of the Background

In general dental diseases have many kinds, some of which are caused by contagious germs. For example the periodontal disease is known. The first thing is, therefore, to identify or ascertain in diagnosis whether or not anaerobic germs are present. In order to identify anaerobic germs they must be cultivated. For this purpose a variety of vessels or receptacles have been proposed. They are commonly devised so as to produce deoxygenated atmosphere. To cultivate anaerobic germs they are taken from the patient's mouth, and planted on a plate. Then the germ-coated plate is sealed, and placed in the anaerobic atmosphere for a long period of time. Anaerobic germiculture receptacles are used for cultivating anaerobic germs, and there are many kinds available in the market.

A typical example is made up of a bag made of a resilient sheet, a culture bed, a deoxidizer, and a $CO_2$ generating agent. The bag inflates with the $CO_2$ gas generating from the agent, and the oxygen is removed so as to produce an anaerobic atmosphere. In this example a great amount of air enters the receptacle when the culture bed is placed therein, which requiring a great deal of deoxidizer. In addition since the bag is flat, it is difficult to secure the culture bed in its even state. To provide the even bed a high degree of skill is required. The $CO_2$ generating agent consists of a solid substance and a liquid substance, which are mixed together when $CO_2$ gas is to be generated. The solid substance and the liquid substance are packed separately in the package, which requires a complicated packaging process. This reflects in the package cost. In such packages it is necessary for the two substances to become mixed by a simple operation. To achieve this purpose the package must be accordingly devised. Furthermore, it is necessary to prevent the mixed substances from leaking outside. After all the receptacle unavoidably becomes complicated in structure and expensive in price.

There is another type of anaerobic germiculture receptacle known in the art, which is provided with a gas inlet and a gas outlet. After the germ-coated plate is placed in the receptacle it is airtightly closed with the lid, and supplied with $CO_2$ gas introduced through the inlet so as to replace the inside air therewith. This type of receptacle requires a gas cylinder and other ancillary devices. In addition, the size of receptacle becomes large. Another disadvantage is that the anaerobic atmosphere cannot always prevail itself in the receptacle, thereby failing to discover anaerobic germs. This leads to an erroneous diagnosis and a wrong medical treatment.

SUMMARY OF THE INVENTION

The present invention aims at solving the problems pointed out with respect to the known anaerobic germiculture receptacles, and has for its object to provide an anaerobic germiculture receptacle of simple construction and capable of easy operation.

Other objects and advantages of the present invention will become apparent from the detailed description given hereinafter; it should be understood, however, that the detailed description and specific embodiment are given by way of illustration only, since various changes and modifications within the spirit and scope of the invention will become apparent to those skilled in the art from this detailed description and drawings.

According to the present invention, there is provided an anaerobic germiculture receptacle, which comprises:

a first cylindrical receptacle having one open end;

a second cylindrical receptacle adapted to be accommodated in the first receptacle, the second receptacle having one open end;

a sealing plug for closing the ope end of the first receptacle, the plug including a bore produced axially thereof and having a size enough to allow the passage of the second receptacle;

a pushing rod insertable in the bore; wherein the open end of the first receptacle is defined by a rim;

wherein the sealing plug includes a shoulder complemental with the rim of the first receptacle; and wherein the bore is enclosed by an inside wall including a plurality of ring-shaped projections.

BRIEF DESCRIPTION OF THE DRAWINGS

FIG. 2a is a vertical cross-section through the receptacle of FIG. 1, and FIGS. 2b and 2c show magnifications of an alternate embodiment of a rim;

FIG. 3a is a fragmentary view on a larger scale of the sealing plug shown in FIG. 1, and FIG. 3b is a magnification of an alternate embodiment of a sealing plug;

FIG. 4 is a plan view of the sealing plug;

FIG. 5a is a vertical cross-section through another example of the embodiment and FIG. 5b is a magnification of an alternate embodiment of a sealing rim.

DETAILED DESCRIPTION OF THE PREFERRED EMBODIMENTS

Figure 1:
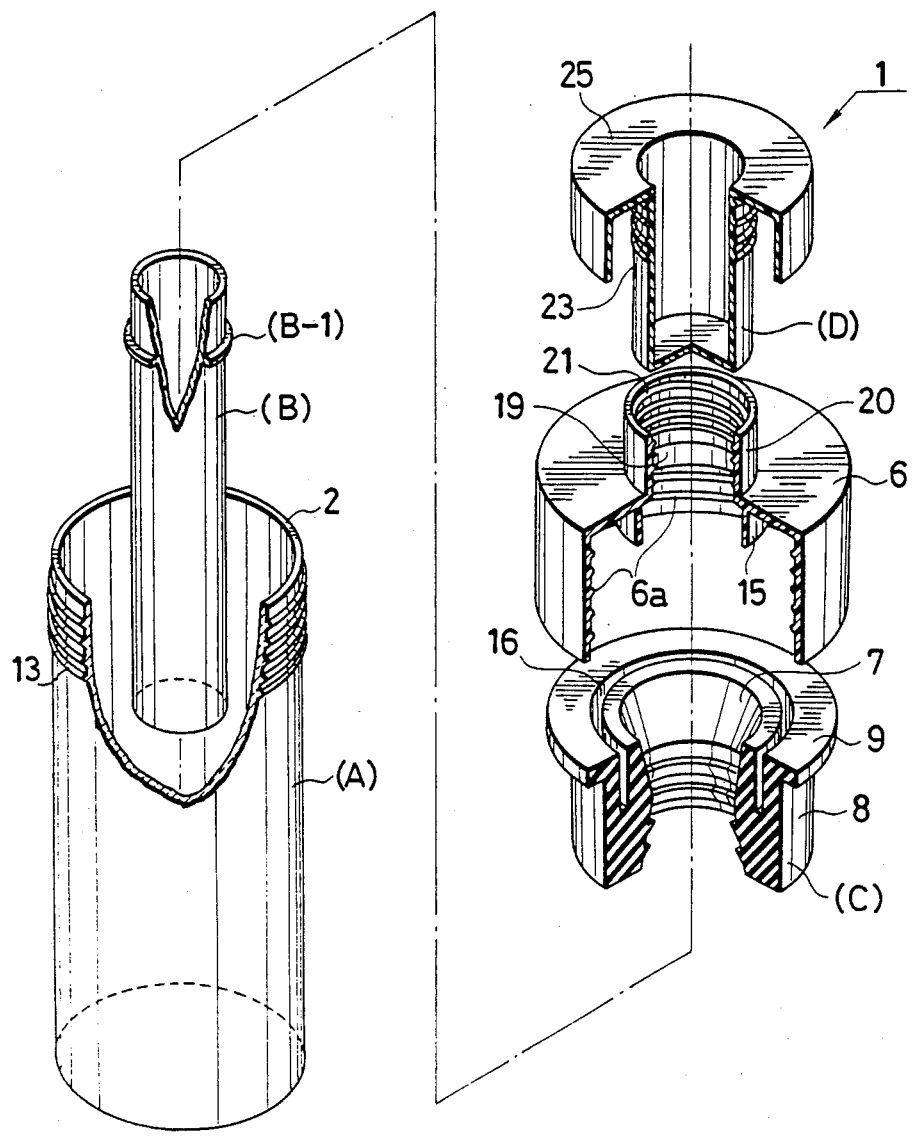
FIG. 1 is a perspective view showing an anaerobic germiculture receptacle embodying the present invention in an analytical state.

Referring to FIGS. 1 and 2, an anaerobic germiculture receptacle, hereinafter referred to as the receptacle, is generally denoted by the reference numeral 1. The receptacle 1 includes a first cylindrical receptacle (A), a second cylindrical receptacle (B), a sealing plug (C), and a pushing rod (D), wherein the first receptacle (A) has a larger diameter than that of the second receptacle (B) so as to allow the latter to be housed in the former. Each of the receptacles (A) and (B) has an open end and a closed bottom, and is normally made of transparent material, such as plastics or glass. The sealing plug (C) is made of an elastic material, such as rubber or plastics. As shown in FIG. 3, the sealing plug (C) includes a bore 7 produced axially thereof. The bore 7 is enclosed by a tapered wall 11 in its upper section, wherein, as clearly shown in FIG. 3, the tapered wall 11 inwardly converges and outwardly diverges so that the pushing rod (D) is readily inserted in the bore 7. The reference numeral 8 denotes a substantial part of the plug (C), hereinafter referred to as the plug body, and the reference numeral 9 denotes a flange, which rests on the rim of the first receptacle (A), whereas the plug body 8 is fitted in the upper portion thereof.

As described above, the flange 9 of the plug (C) rests on the rim of the first receptacle, wherein, as clearly shown in FIG. 2, the rim 2 is inwardly tapered or has a flat surface which is perpendicular to the axis of the receptacle (see FIGS. 2 and 3). This geometry insures liquid-tightness. The flange 9 has a shoulder 5 which is tapered or flat and perpendicular to the axis of the recepticle so as to be complemental with the rim 2 of the receptacle (A). When the first receptacle (A) is covered by a lid 6, and threads 6a, 13 are engaged, both faces 2 and 5 are tightly engaged, thereby ensuring that the first receptacle (A) is sealed by the plug (C). As evident from FIG. 2, the threads 6a are produced on the inside of the lid 6 and the threads 13 are produced on the outside of the upper section of the receptacle (A). In a preferred embodiment, the flat rim of the first receptacle is provided with an annular bead projecting from the flat rim. The annular bead provides for optimum sealing when contacted with the complementary flat shoulder of flange 9 of the plug (C). This embodiment is illustrated in the enlarged representation of the area within the phantom circle shown in FIG. 2.

As described above, the bore 7 is enclosed by the inwardly tapered wall 11 in its upper section. Whereas, in its lower section it is enclosed by an outwardly tapered wall 12. This lower section of the bore 7 holds the second receptacle (B). To effect the holding of the second receptacle the tapered wall 12 is provided with a plurality of ring-shaped tapered projections; in the illustrated embodiment, two projections 10a and 10b are provided. The ring-shaped grooves 10a and 10b in the bore 7 have diminishing diameters toward the upper open end so that the second (smaller) receptacle (B) is easily inserted into the bore 7 from the lower open end (see FIG. 3). In addition, the inserted second receptacle is prevented from coming out of the bore 7 unless it is forced down by a bar or the like. The ring-shaped projections 10a, 10b ensures the seal between the plug (C) and the second receptacle (B). The reference character (B)-1 denotes a stop for preventing the second receptacle (B) from being excessively inserted in the bore 7. After the air in the first receptacle (A) is replaced by nitrogen, it is sealed by the plug (C). Then the second receptacle (B) held in the bore 7 is caused to drop toward the bottom of the first receptacle. In this process the seal between the plug and the second receptacle (B) prevents outside air from entering the receptacle 1.

The lid 6 is provided with a cylindrical inner wall 15, which is fitted in a ring-shaped groove 16 produced in the plug body 8. When the inner wall 15 is inserted in the groove 16, the plug body 8 is outwardly expanded, thereby securing the seal between the plug (C) and the first receptacle (A). The ring-shaped groove 16 may be provided with ridges 17 produced axially of the plug (C). Alternatively they can be produced on the outside of the cylindrical inner wall 15. The ridges 17 ensure the joint between the lid 6 and the plug (C). In the embodiment shown in FIG. 4 three ridges 17 are given but the number of them is not limited to it.

The lid 6 includes an aperture 19 produced so as to be coaxial with the bore 7 when the lid 6 is placed on the first receptacle (A). The reference numeral 20 denotes a boss, through which the pushing rod (D) is movably inserted. The reference numerals 21 and 23 denote threads produced on the inside of the boss 20 and the outside of the pushing rod (D), respectively. These threads are engaged when the pushing rod (D) is inserted into the boss. The pushing rod (D) is provided with a knob 25, whereby the pushing rod (D) is turned so as to enable the pushing rod to sink into the aperture 19 and the bore 7. In FIG. 2 the reference numeral 28 denotes an ampoule in which a culture bed 29 (as of agar-agar or liquid) is located.

Referring to FIG. 1 the receptacle 1 of the invention is assembled in the following manner:

The assembling is carried out under an oxygen-free atmosphere, such as a mixed-gas atmosphere containing 90% of nitrogen gas and 10% of carbon dioxide gas, and in an aseptic condition. First, a deoxidizer 27 (for example, ferrous oxide), and when necessary, a $CO_2$ generating agent are placed in the first receptacle (A). The deoxidizer 27 is used to remove oxygen but the method of removing it is not limited to the use of a deoxidizer, which will be described below. Then the second receptacle (B) is inserted into the bore 7 along the tapered wall 12 until the stop (B)-1 comes into abutment with the plug body 8. The sealing plug (C) having the second receptacle (B) is fitted in the first receptacle (A). Then the first receptacle (A) is covered by the lid 6, and the pushing rod (D) is screwed into the boss 20 by turning the knob 25 until the top end of the rod comes into abutment with the second receptacle (B) or comes at a position slightly spaced therefrom. At this stage the second receptacle (B) is not yet sealed. In this state the receptacle 1 is supplied to dentists. The air in the two receptacles (A) and (B) is replaced by nitrogen beforehand. The nitrogen atmosphere therein is safely kept by the sealing arrangements between the plug and the first receptacle (A) and between the plug and the second receptacle (B).

In this way the receptacle 1 is prepared. To identify the germs taken from the patient's mouth they are collected by the use of a platina spatula, and planted on the culture bed 29 previously laid in the ampoule 28. The ampoule 28 is previously filled with nitrogen. When the germs are to be planted on the culture bed 29, the head portion of the ampoule 28 is cut away, and after the plantation is finished, the cut head is covered by a cap 28a, which is left loose at this stage. This operation is carried out in the atmosphere, and it is unavoidable to allow outside air to become admixed with the filled nitrogen in the receptacles (B) and the ampoule 28 to some extent. As a result the atmosphere for the culture bed 29 is not perfectly anaerobic. After the germs are planted on the bed 29, the pushing rod (D) is immediately inserted into the bore 7, so as to prevent outside air from entering the receptacle (B) as shown in FIG. 2. The pushing rod (D) is further pushed until the second receptacle (B) falls onto the bottom of the first receptacle (A). While the second receptacle (B) is descending the seal with the plug (C) is maintained by virtue of the ring-shaped projections 10a and 10b, thereby preventing a detrimental amount of air from entering the receptacle (B).

Subsequently the air in the ampoule 28 and the receptacle (B) is replaced by nitrogen, and the oxygen therein is removed by the deoxidizer 27. In this way the oxygen in the receptacle (A) is removed until the anaerobic atmosphere is restored, in which the culture bed 29 is left at a given temperature for a given period of time. Then the germs are identified or ascerained. The amount of the deoxidizer 27 is determined so that it can absorb all oxygen in the air which presumably fills the receptacle to its full capacity.

In the foregoing example the seal between the first receptacle (A) and the plug (C) is effected by the lid 6. The shape and structure of the lid 6 is not limited to the illustrated embodiment; one of the modifications is shown in FIG. 5:

The modified lid has a foldable rim 30 shown by dotted lines, which is folded outward into a state indicated by 30a. FIG. 5 is a schematic view, having the tapered or perpendicular rim 2, the tapered or perpendicular shoulder 5 and the ring-shaped projections 10a, 10b are omitted for simplicity.

Figure 6:
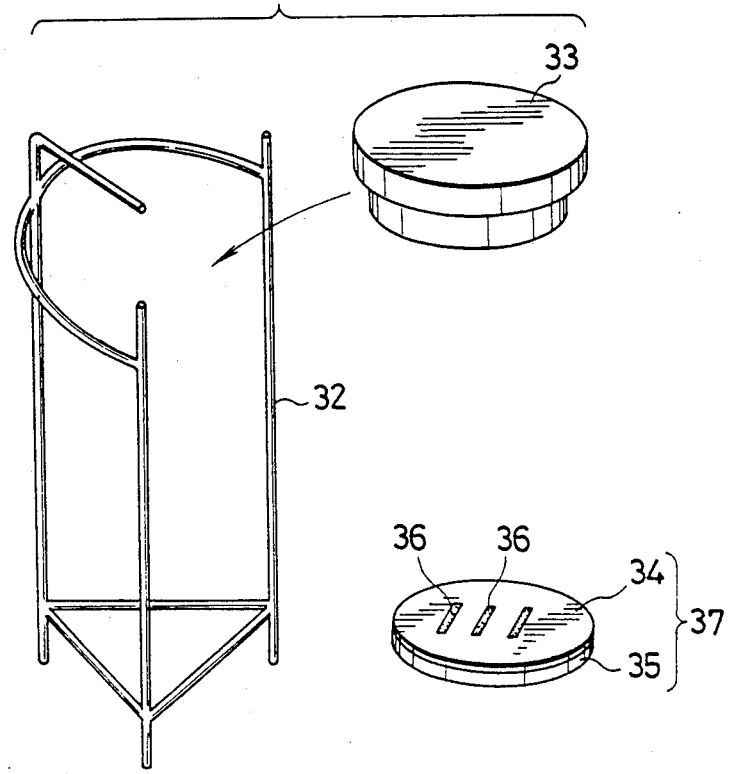
FIG. 6 is an analytical perspective view showing a suport member, a Petri dish and a deoxidizing and $CO_2$ generating sheet.

FIG. 6 shows another method of using the anaerobic germiculture receptacle 1. Several Petri dishes 33 (for example, four dishes) are placed one above another on a rack 32, such as a wirework, wherein each dish contains a culture bed. Then the rack 32 having the dishes 33 is placed in the first receptacle (A). The reference numeral 37 denotes a deoxygenating and $CO_2$ gas generating sheet, invented by the same inventor, for which Patent Application No. 59(1984)-202271 is pending. This sheet 37 can be used when the rack 32 is placed in the receptacle (A). The sheet 37 is made up of a hydrophobic layer 34 and a body layer 35, which comprises a sheet of cellulose fiber, impregnated with a deoxidizing and $CO_2$ gas generating agent, such as sodium L-ascorbic acid and hepta-aqua ferrous sulphate. The hydrophobic layer 34 is to prevent the deoxidizing and $CO_2$ gas generating agent in a liquid state from keeping contact with an oxygen indicating ink layer or oxygen detecting layer 36, and diffusing therethrough. The oxygen detecting layer 36 facilitates the observation of an anaerobic condition in the receptacle 1, and the ascertaining of a possible operation error. The receptacle 1 is used in combination with the device shown in FIG. 6, which will make the present invention more applicable to a variety of purposes.

The anaerobic atmosphere can be produced by other methods than those described above, for example:

(1) By using a glass wool impregnated with copper, or a deoxidizing agent, such as activated carbon;

(2) By confining hydrogen and placing a suitable catalyst in the receptacle 1 beforehand, and causing the hydrogen to react with the oxygen therein on the catalyst, thereby removing the oxygen (alternatively, nitrogen can be confined, and any hydrogen generating agent can be used instead of using a hydrogen gas); or (3) By producing a nitric atmosphere, and burning phosphorus therein, thereby removing the oxygen in the receptacle 1.

An example of the oxygen indicating or detecting ink is disclosed in Japanese Utility Model Publication (unexamined) No. 60(1985)-144931. The ink is applied to the hydrophobic film.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An anaerobic germiculture receptacle comprising:
    a first cylindrical receptacle having one open end; a second cylindrical receptacle adapted to be accommodated in the first receptacle, the second receptacle having one open end;
    a sealing plug for closing the open end of the first receptacle, the plug including a bore produced axially thereof and having a size enough to allow the passage of the second receptacle;
    a pushing rod insertable in the bore; wherein the open end of the first receptacle is defined by a flat rim, said flat rim being provided with an annular bead projecting from said flat rim for sealing by said sealing plug; and
    a lid including an aperture produced coaxially of the bore of the sealing plug, the lid being adapted to cover the sealing plug airtightly;
    wherein the sealing plug includes a flat shoulder complimental with the rim of the first receptacle, the sealing plug includes a ring-shaped groove, and the lid includes a cylindrical inner wall fitted in the ring-shaped groove of the sealing plug; and
    wherein the bore is defined by an inside wall including a plurality of ring-shaped projections.

2. The anaerobic germiculture receptacle of claim 1, wherein the ring-shaped groove or the cylindrical inner wall is provided with a plurality of ridges produced axially of the sealing plug, thereby increasing the sealing effect of the plug against the lid.

* * * * *